United States Patent
Vane et al.

(10) Patent No.: US 6,647,294 B2
(45) Date of Patent: *Nov. 11, 2003

(54) HIGH-SIDE ENERGY DELIVERY THROUGH A SINGLE-QUADRANT THYRISTOR TRIGGERED WITH A CURRENT-LIMITING SWITCH

(75) Inventors: Mark Vane, Minneapolis, MN (US); Kristofer J. James, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 101 days.

This patent is subject to a terminal disclaimer.

(21) Appl. No.: 09/966,643

(22) Filed: Sep. 28, 2001

(65) Prior Publication Data

US 2002/0013610 A1 Jan. 31, 2002

Related U.S. Application Data

(63) Continuation of application No. 09/525,487, filed on Mar. 15, 2000, now Pat. No. 6,311,087.

(51) Int. Cl.[7] .................................................. A61N 1/39
(52) U.S. Cl. ............................................................. 607/5
(58) Field of Search ....................................... 607/1–76

(56) References Cited

U.S. PATENT DOCUMENTS

| | | | |
|---|---|---|---|
| 4,088,138 A | 5/1978 | Diack et al. ................. 128/419 |
| 4,285,345 A | 8/1981 | Mensink et al. ............. 128/419 |
| RE30,750 E | 9/1981 | Diack et al. ................. 128/419 |
| 4,850,357 A | 7/1989 | Bach, Jr. ................. 128/419 D |
| 4,998,531 A | 3/1991 | Bocchi et al. .......... 128/419 D |
| 5,033,467 A | 7/1991 | Bocchi et al. .............. 128/419 |
| 5,111,816 A | 5/1992 | Pless et al. ........... 128/419 PG |
| 5,305,745 A | 4/1994 | Zacouto ...................... 128/637 |
| 5,336,253 A | 8/1994 | Gordon et al. .............. 607/122 |
| RE34,879 E | 3/1995 | Bocchi et al. .................. 607/5 |
| 5,468,254 A | 11/1995 | Hahn et al. ..................... 607/5 |
| 5,722,994 A | 3/1998 | Noren et al. .................... 607/5 |
| 6,023,638 A | 2/2000 | Swanson .................... 600/510 |

Primary Examiner—Scott M. Getzow
(74) Attorney, Agent, or Firm—Schwegman, Lundberg, Woessner & Kluth, P.A.

(57) ABSTRACT

A cardiac rhythm management system includes an implantable cardiac rhythm management device that includes a defibrillation energy delivery circuit. The defibrillation energy delivery circuit provides high side energy delivery through a single-quadrant thyristor switch that is triggered by a current-limiting transistor switch. The defibrillation energy delivery circuit requires fewer electronic components, reducing the size and/or cost of the implantable cardiac rhythm management device. For example, the single-quadrant thyristor, designed to conduct and latch in only one quadrant (e.g., quadrant III) and having appropriate dV/dt and voltage blocking capabilities, may eliminate the need for additional series-coupled semiconductor devices. In another example, current-limiting is designed into, or inherent in, the semiconductor device triggering the single-quadrant thyristor, thereby eliminating the need for additional current-limiting circuits.

27 Claims, 4 Drawing Sheets

HIGH-SIDE ENERGY DELIVERY THROUGH A SINGLE-QUADRANT THYRISTOR TRIGGERED WITH A CURRENT-LIMITING SWITCH

CROSS REFERENCE TO RELATED APPLICATION(S)

This application is a continuation of U.S. patent application Ser. No. 09/525,487, filed on Mar. 15, 2000 now U.S. Pat. No. 6,311,087, the specification of which is incorporated herein by reference.

TECHNICAL FIELD

The present system relates generally to a system delivering high voltage energy, and particularly, but not by way of limitation, to a cardiac rhythm management system including a defibrillation energy delivery circuit having a high-side energy delivery through a single-quadrant thyristor triggered with a current-limiting switch.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Anti-arrhythmic drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Portions of such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock ("shock"). The shock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is in delivering the high energy defibrillation shock. In one example, a transformer-coupled dc-to-dc voltage converter transforms a battery voltage (e.g., battery voltages approximately between 1.5 Volts and 6.5 Volts) up to a high defibrillation voltage (e.g., defibrillation voltages up to approximately 1000 Volts). The energy associated with this high defibrillation voltage is typically stored on a storage capacitor. A defibrillation energy delivery circuit delivers the defibrillation energy from the storage capacitor to defibrillation leadwires and defibrillation electrodes associated with the heart. Upon receiving this defibrillation energy via the defibrillation electrodes, the heart resumes normal rhythms if the defibrillation therapy is successful.

The defibrillation energy delivery circuit typically includes numerous discrete electronic components that must be capable of withstanding the large voltages associated with the defibrillation energy being delivered. These numerous discrete electronic components in the defibrillation energy delivery circuit occupy considerable space in the implantable cardiac rhythm management device. In order to improve patient comfort and aesthetics, however, the implantable cardiac rhythm management device should be small sized. Thus, a need exists for, among other things, reducing the size and/or cost of the defibrillation energy delivery circuit.

SUMMARY OF THE INVENTION

This document describes, among other things, portions of a cardiac rhythm management system including an implantable cardiac rhythm management device that includes a defibrillation energy delivery circuit. The defibrillation energy delivery circuit provides high side energy delivery through a single-quadrant thyristor switch that is triggered by a current-limiting transistor switch. The defibrillation energy delivery circuit requires fewer electronic components, reducing the number of assembly processing steps, cost and physical size of the implantable cardiac rhythm management system. For example, the single-quadrant thyristor is designed for conduction/latching in a single quadrant (e.g., quadrant III) and provides the necessary voltage blocking capabilities that can be used to eliminate the need for additional series coupled voltage blocking semiconductor devices. In another example, current-limiting is designed into, or inherent in, the semiconductor device triggering the single-quadrant thyristor, thereby eliminating the need for additional current-limiting circuits.

This document describes, among other things, a cardiac rhythm management system. In one embodiment, the cardiac rhythm management system includes a cardiac rhythm management device. The cardiac rhythm management device includes a defibrillation energy delivery circuit. The defibrillation energy delivery circuit includes a first input terminal, receiving a first power supply, and a first single-quadrant thyristor, coupled between the first input terminal and a first output terminal.

In another embodiment, the cardiac rhythm management system includes a defibrillation energy delivery circuit. The defibrillation energy delivery circuit includes a first input terminal, receiving a first power supply. The defibrillation energy delivery circuit also includes a first switch, coupled between the first input terminal and a first output terminal. The defibrillation energy delivery circuit further includes a first current-limiting field-effect transistor (FET), coupled to the gate terminal of the first switch and sinking a triggering current.

This document also describes, among other things, a method of delivering defibrillation energy. The method includes receiving an input voltage, triggering a thyristor enabling single-quadrant conduction/latching, and coupling the input voltage to an output terminal using the enabled thyristor. These and other aspects of the present system and methods will become apparent upon reading the following detailed description and viewing the accompanying drawings that form a part thereof.

DETAILED DESCRIPTION OF THE EMBODIMENTS

Figure 1:
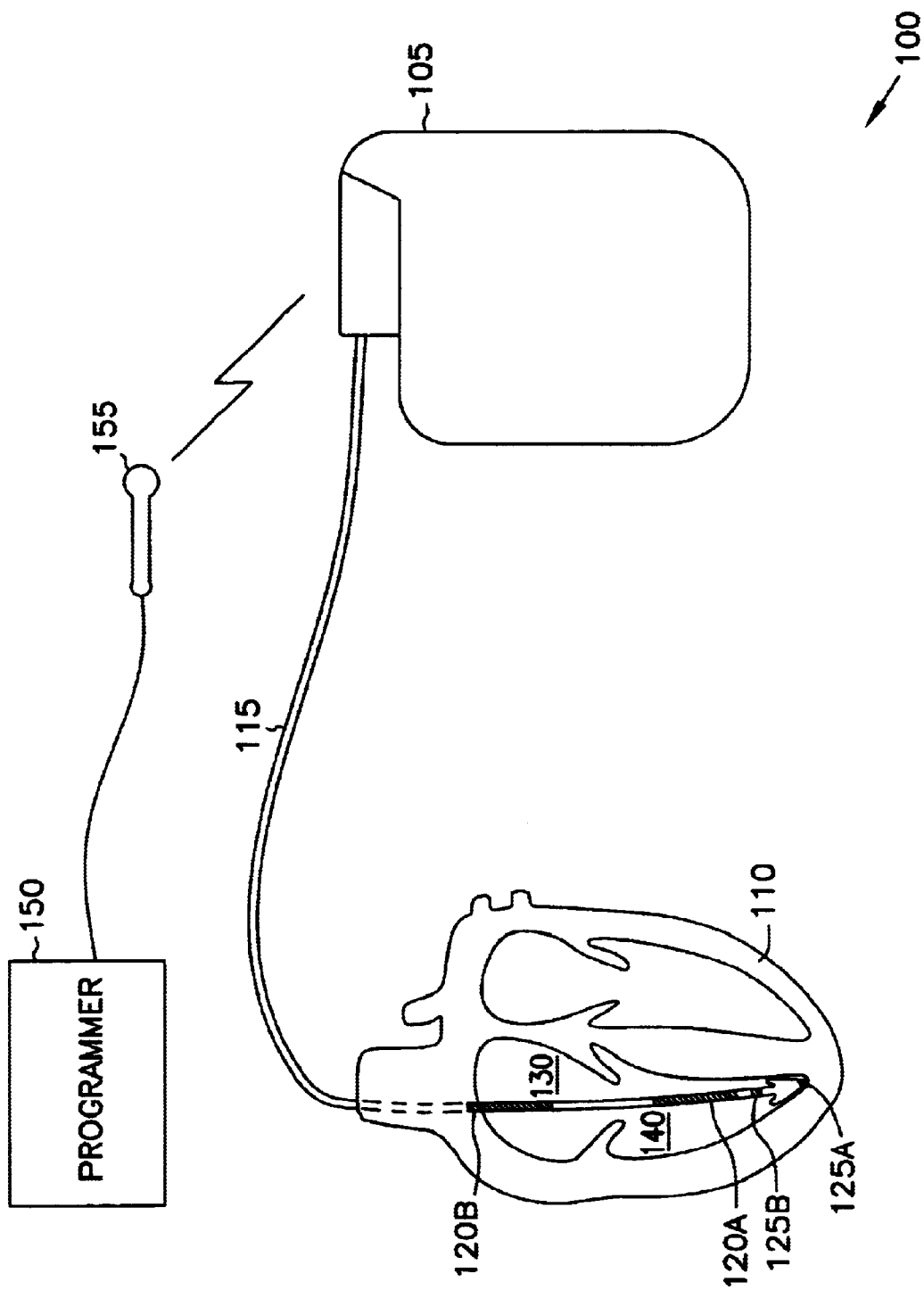
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. In this document, "and/or" refers to non-exclusive "or" (e.g., "A and/or B" includes each of "A but not B," "B but not A," and "A and B").

The present methods and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

General System Overview and Examples

This document describes, among other things, high-side energy delivery through a single-quadrant thyristor triggered with a current limiting switch. The present cardiac rhythm management (CRM) system provides, among other things, an implantable CRM device. The CRM device includes a defibrillation energy delivery circuit capable of delivering high energy using fewer electronic components. This allows a smaller sized CRM device.

FIG. 1 is a generalized schematic diagram illustrating generally, by way of example, but not by way of limitation, one embodiment of a portion of a CRM system 100. Various embodiments of system 100 include external or implantable pacer/defibrillators, cardioverters, defibrillators, any combination of the foregoing, or any other system using or maintaining cardiac rhythms.

In the embodiment of FIG. 1, CRM system 100 includes a CRM device 105 coupled to heart 110 via one or more endocardial or epicardial leadwires, such a pacing leadwire or a defibrillation leadwire 115. Defibrillation leadwire 115 includes one or more defibrillation electrodes, such as for delivering defibrillation countershock ("shock") therapy via first defibrillation electrode 120A and/or second defibrillation electrode 120B. Defibrillation leadwire 115 may also include additional electrodes, such as for delivering pacing therapy via first pacing electrode 125A (e.g., a "tip" electrode) and/or second pacing electrode 125B (e.g., a "ring" electrode). Defibrillation electrodes 120A–B and pacing electrodes 125A–B are typically disposed in or near one or more chambers of heart 110.

In the embodiment of FIG. 1, defibrillation leadwire 115 includes multiple conductors that are insulated from each other for providing independent connections between each electrode and cardiac rhythm management device 105. In one embodiment, the defibrillation leadwire is secured to heart 110, such as by a corkscrew, a barb, or similar mechanism at or near first pacing electrode 125A. In another embodiment, CRM device 105 includes a hermetically sealed casing, a portion of which provides a conductive electrode that operates in conjunction with at least one of the electrodes disposed in heart 110 for delivering pacing pulses and/or defibrillation countershocks and/or sensing electrical heart activity signals.

In one embodiment, CRM system 100 includes a remote user interface, such as programmer 150, which permits communication with CRM device 105 using telemetry wand 155 or other communication device. Programmer 150 provides information to a physician or other caregiver, such as using a graphical user interface on a screen display, or providing data using a strip chart recorder, or by any other technique. Programmer 150 also receives user input, such as for programming and/or controlling the functionality of programmer 150 and/or CRM device 105.

Example Cardiac Rhythm Management Device

Figure 2:
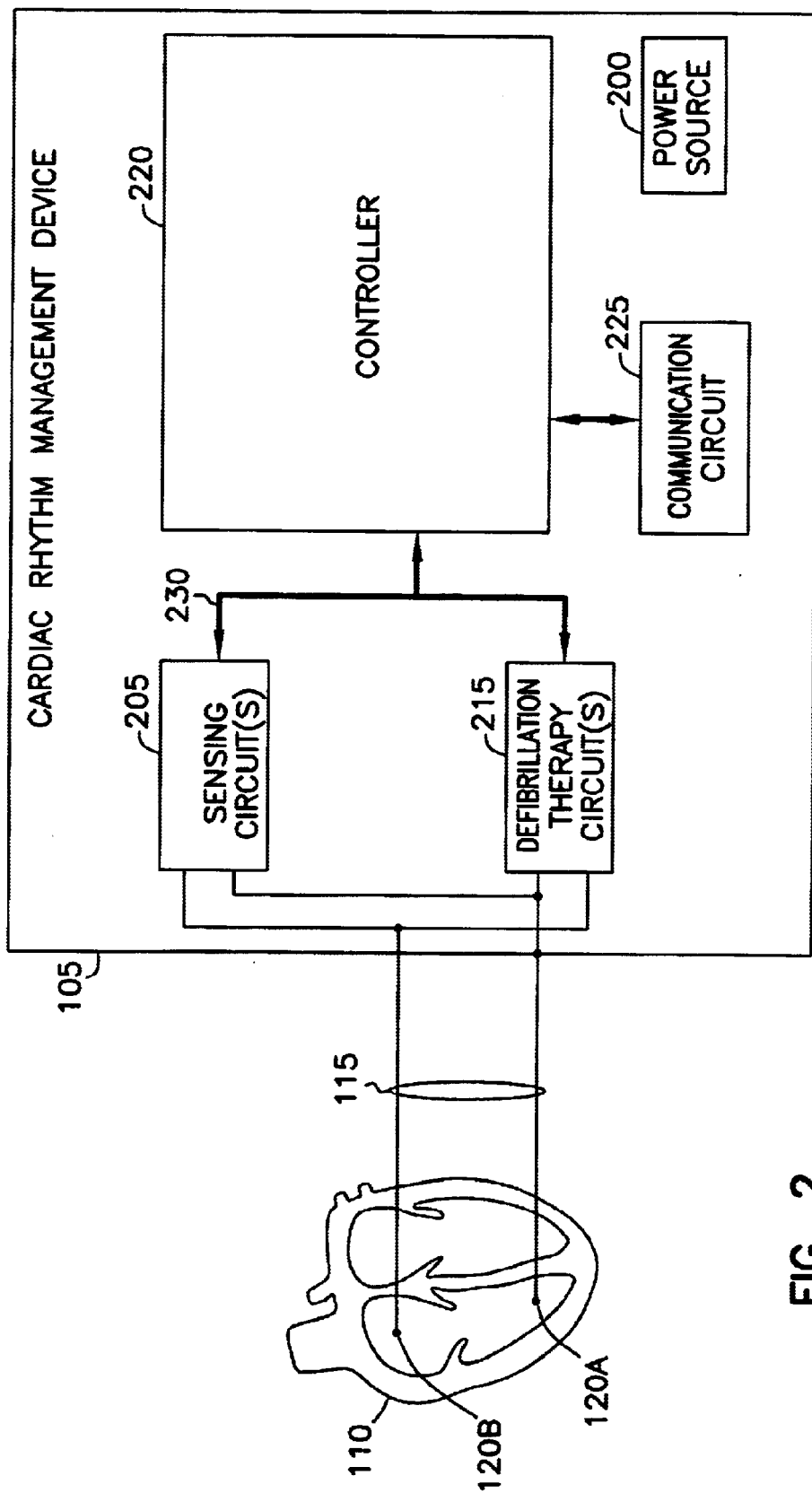
FIG. 2 is a schematic drawing illustrating generally one embodiment of a cardiac rhythm management device, which is coupled to a heart, and certain aspects of the device.

FIG. 2 is a schematic diagram illustrating generally, by way of example, but not by way of limitation, one embodiment of portions of device 105, which is coupled to heart 110. Device 105 includes a power source 200, heart signal sensing circuit(s) 205, defibrillation therapy circuit(s) 215, a controller 220, and a communication circuit 225 for communicating with programmer 150 via telemetry device 155.

The heart signal sensing circuits 205 are coupled by one or more leads 115 to one or more electrodes associated with heart 110 for receiving, sensing, and/or detecting electrical heart signals. Such atrial and/or ventricular heart signals correspond to heart contractions. Such heart signals include normal rhythms, and abnormal rhythms including tachyarrhythmias, such as fibrillation, and other activity. Atrial sensing circuit 205 provides one or more signals to controller 220, via node/bus 230, based on the received heart signals.

In one embodiment, defibrillation therapy circuit(s) 215 provide cardioversion/defibrillation therapy, as appropriate, to the heart electrodes 120A–B. Controller 220 controls the delivery of defibrillation therapy by defibrillation therapy circuit(s) 215 based on heart activity signals received by sensing circuit(s) 205. Controller 220 may further control the delivery of pacing therapy such as by a pacing therapy circuit (not shown) via pacing electrodes 125A–B. Controller 220 includes various modules, which are implemented either in hardware or as one or more sequences of steps carried out on a microprocessor or other controller. Such modules may be conceptualized separately, but it is understood that the various modules of controller 220 need not be separately embodied, but may be combined and/or otherwise implemented, such as in software/firmware.

In general terms, sensing circuit(s) 205 sense electrical signals from heart tissue in contact with the catheter lead(s) 115 to which sensing circuit(s) 205 are coupled. Sensing circuit(s) 205 and/or controller 220 process these sensed signals. Based on these sensed signals, controller 220 issues control signals to therapy circuit 215, if necessary, for the delivery of electrical energy (e.g., defibrillation pulses) to the appropriate electrodes of lead 115. Controller 220 may include a microprocessor or other controller for execution of software and/or firmware instructions. The software of controller 220 may be modified (e.g., by remote external programmer 150) to provide different parameters, modes, and/or functions for the implantable device 105 or to adapt or improve performance of device 105.

Figure 3:
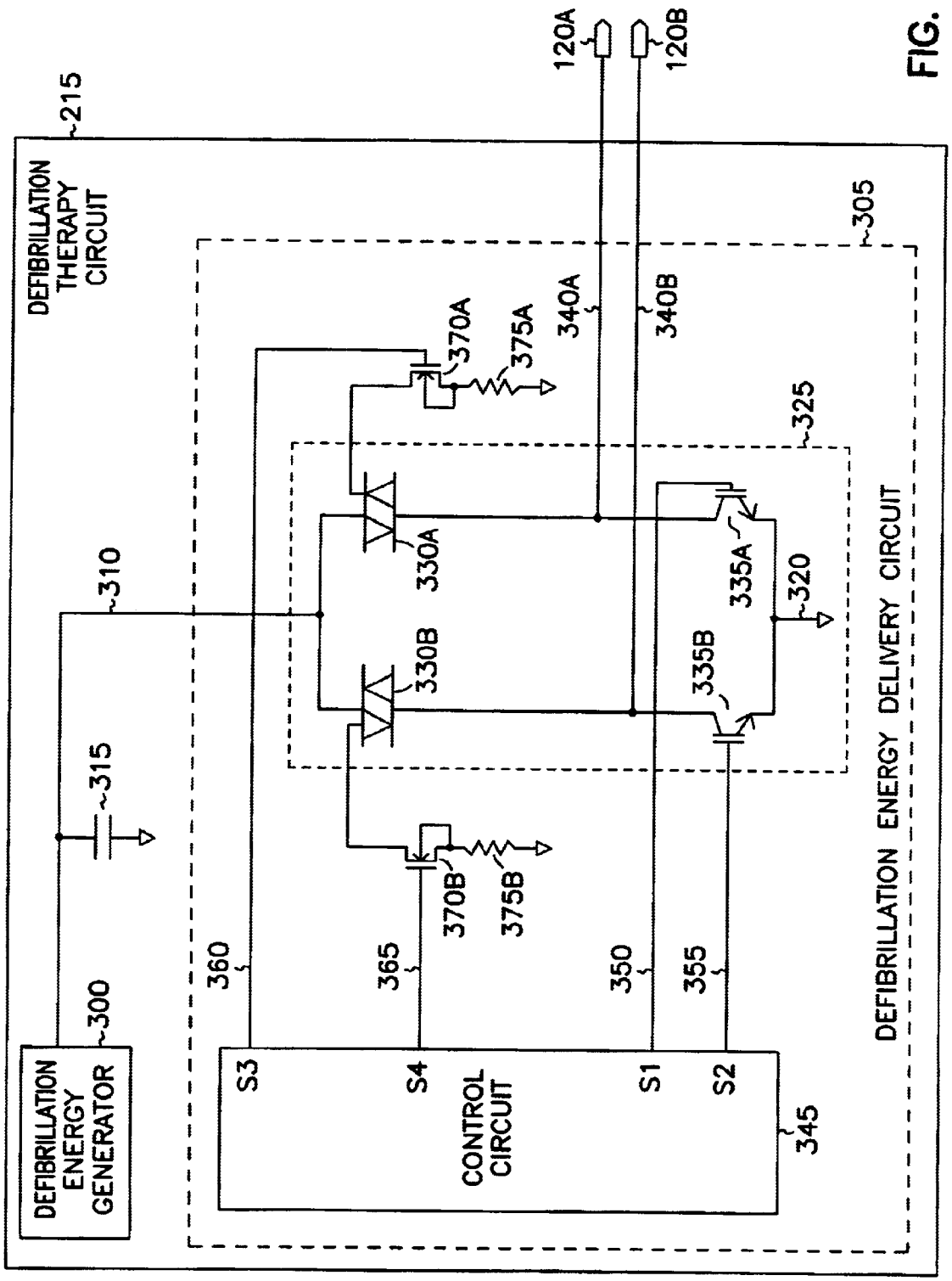
FIG. 3 is a schematic/block diagram illustrating generally one conceptual embodiment of portions of a defibrillation therapy circuit.

FIG. 3 is a schematic/block diagram illustrating generally, by way of example, but not by way of limitation, one conceptual embodiment of portions of defibrillation therapy circuit 215. In this embodiment, defibrillation therapy circuit 215 includes a defibrillation energy generator circuit 300 and a defibrillation energy delivery circuit 305. In one example, defibrillation energy generator 300 includes a transformer-coupled dc-to-dc voltage converter that transforms a voltage provided by power source 200 (e.g., source voltages of approximately between 1.5 Volts and 6.5 Volts) up to a high defibrillation voltage (e.g., defibrillation voltages up to approximately 1000 Volts) at node 310. The energy associated with this high defibrillation voltage is typically stored on a defibrillation energy storage capacitor 315 until delivered to heart 110 via defibrillation energy delivery circuit 305 and defibrillation electrodes 120A–B. While the defibrillation voltages of up to approximately 1000 Volts generally describes current applications, defibrillation voltages may often fall within the range of approximately 600 to 800 Volts, such as approximately 780 Volts or approximately 645 Volts. Regardless, the various embodiments of the invention are not limited by such defibrillation voltages and may be adapted to other voltages.

Defibrillation energy delivery circuit 305 includes a first input terminal that receives a first power supply voltage (e.g., the voltage associated with the defibrillation energy at node 310) and a second input terminal that receives a second power supply voltage (e.g., the ground voltage at node 320). Energy delivery circuit 305 includes an H-bridge 325, which includes four switches (i.e., first and second pull-up switches 330A–B and first and second pull-down switches 335A–B) for coupling the defibrillation energy at node 310 and the ground voltage at node 320 to first and second output terminals at nodes 340A–B, respectively. Nodes 340A–B are coupled to defibrillation electrodes 120A–B, respectively.

Pull-up switches 330A–B couple the defibrillation energy at node 310 to respective first and second output terminals at nodes 340A–B, respectively. Pull-down switches 335A–B couple the ground voltage at node 320 to respective first and second output terminals at nodes 340A–B, respectively. In one embodiment, for delivering a monophasic defibrillation energy pulse, control circuit 345 (which can alternatively be conceptualized as part of controller 220) turns on pull-down switch 335A, then turns on pull-up switch 330B. To discontinue energy delivery, control circuit 345 turns off pull-down switch 335A, thus turning off pull-up switch 330B. To further deliver a biphasic defibrillation energy pulse, control circuit 345 then turns on pull-down switch 335B, then turns on pull-up switch 330A. To discontinue energy delivery, control circuit 345 then turns off pull-down switch 335B, thus turning off pull-up switch 330A. Multiphasic energy delivery may be generated by repeating the cycle of delivering and discontinuing an energy pulse in similar fashion for three or more cycles. It is thus inherent that the two cycles of biphasic energy delivery are a subset of the three or more cycles of multiphasic energy delivery. In one embodiment, the user can select between monophasic, biphasic or multiphasic energy delivery using programmer 150 to program device 105 to operate accordingly.

In one embodiment, by way of example, but not by way of limitation, pull-down switches 335A–B include insulated gate bipolar transistors (IGBTs) or other switching devices that couple the respective first and second defibrillation electrodes 120A–B to ground node 320. In one embodiment, first pull-down switch 335A includes a collector coupled to first defibrillation electrode 120A, a gate coupled to receive control signal S1 at node 350 from control circuit 345, and an emitter coupled to ground node 320. Second pull-down switch 335B includes a collector coupled to second defibrillation electrode 120B, a gate coupled to receive control signal S2 at node 355 from control circuit 345, and an emitter coupled to ground node 320.

In one embodiment, by way of example, but not by way of limitation, first and second pull-up switches 330A–B include triacs, thyristors, semiconductor-controlled rectifiers (SCRs), semiconductor-controlled switches (SCSs), four-layer diodes or other switching devices that couple the high voltage associated with the defibrillation energy at node 310 to first and second defibrillation electrodes 120A–B, respectively. In one embodiment, control signals S3 and S4 are received at nodes 360 and 365, respectively, from control circuit 345 to initiate operation of first and second pull-up switches 330A–B, respectively. In one embodiment, control signals S3 and S4 activate triggering devices 370A–B, which provide triggering signals to the gates of switches 330A–B, respectively.

In a further embodiment, first and second pull-up switches 330A–B include single-quadrant thyristors. A triac (also referred to as a bilateral triode switch) typically latches into a conducting state in three quadrants of the four quadrants in its current vs. voltage graph. FIG. 4A is a graph illustrating generally, by way of example, but not by way of limitation, one embodiment of a portion of a current vs. voltage characteristic of a triac, with the four quadrants labeled I, II, III, and IV. Each of quadrants I, II, and III include a resistive/blocking state 405 (indicated by a portion of the curve running approximately parallel to the voltage axis) and a conductive/latching state 410 (indicated by a portion of the curve running approximately parallel to the current axis). An appropriate trigger current, $I_G$, to the gate of the triac reduces the breakover voltage magnitude $v_{bo}$ between the resistive and conductive states, allowing the triac to latch into the conductive state. The solid lines generally depict breakover voltage at a trigger current of zero. The dashed lines generally depict the effect on breakover voltage at a trigger current of magnitude greater than zero (absolute value greater than zero for quadrant I and absolute value less than zero for quadrants II and III).

Figure 4B:
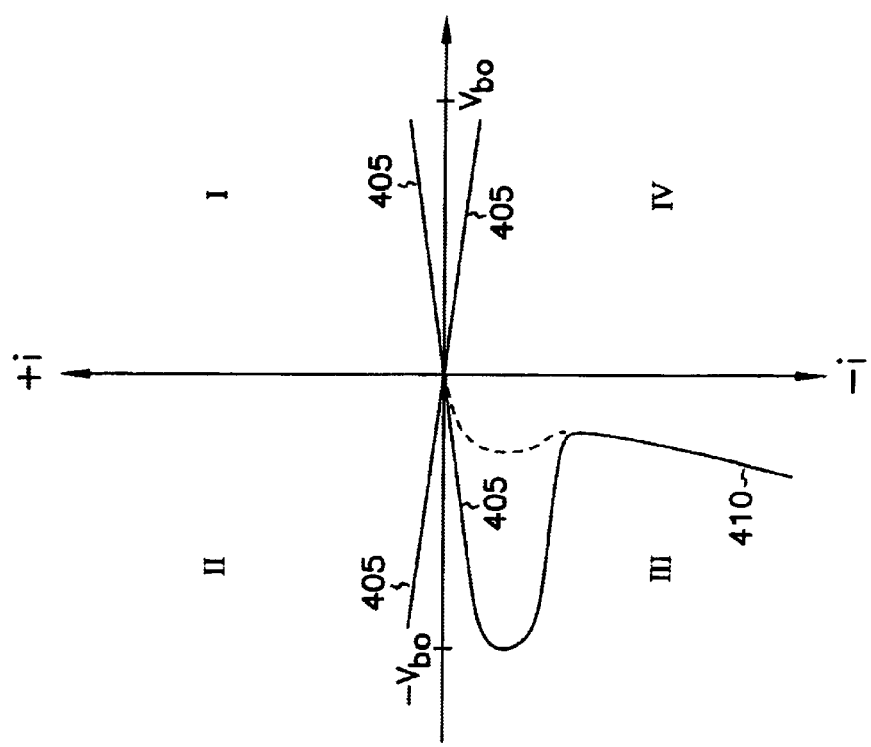
FIG. 4B is a graph illustrating generally one embodiment of a portion of a current vs. voltage characteristic of a single-quadrant thyristor, with the four quadrants labeled I, II, III, and IV.
Figure 4A:
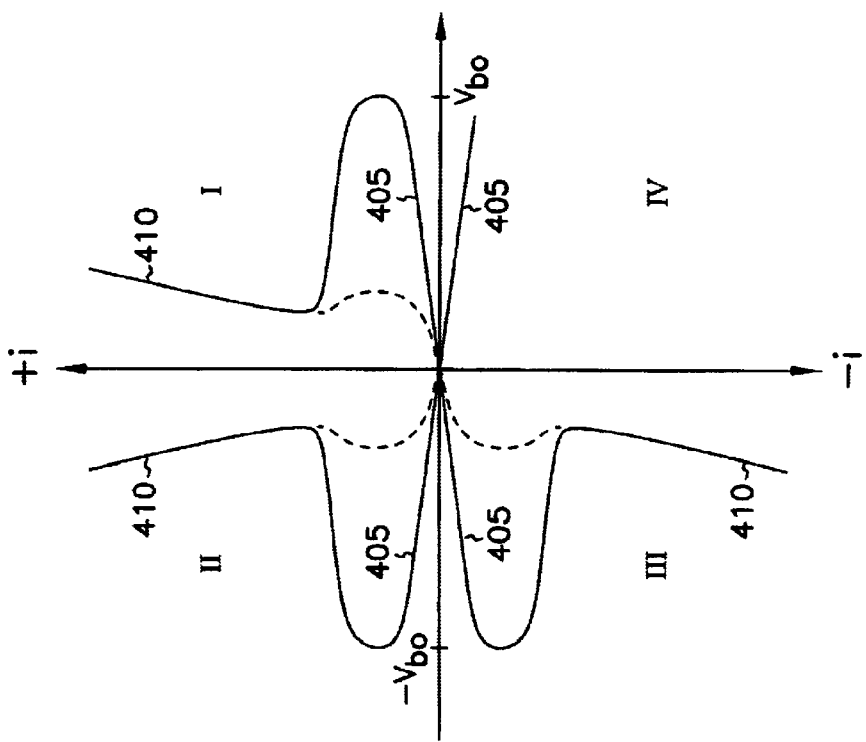
FIG. 4A is a graph illustrating generally one embodiment of a portion of a current vs. voltage characteristic of a triac, with the four quadrants labeled I, II, III, and IV.

By contrast, FIG. 4B is a graph illustrating generally, by way of example, but not by way of limitation, one embodiment of a portion of a current vs. voltage characteristic of a single-quadrant thyristor. Only the third quadrant, quadrant III, includes both a resistive/blocking state 405 and a conductive/latching state 410 within the range of trigger currents as described herein. Quadrants I, II, and IV include only resistive/blocking states (although it is understood that quadrant II could have a conductive region, albeit without latching; this is implied, but not shown in FIG. 4B). It is also understood that single-quadrant thyristors for use with the various embodiments of the invention could provide a conductive/latching state using quadrants other than the exemplary third quadrant without departing from the scope of the teachings of this document, provided only one quadrant of the single-quadrant thyristor includes both a resistive/blocking state and the conductive/latching state as described herein.

The gate triggering current for which it is designed latches the single-quadrant thyristor in a conductive/latching state in essentially only one quadrant of the current vs. voltage characteristic graph. It is understood that it may be possible to conduct through the single-quadrant thyristor in other quadrants as well, but that a substantially larger gate triggering current, i.e., exceeding device ratings, is required to initiate conduction in those other quadrants. Stated differently, triggering devices 370A–B are designed to sink a trigger current from the gates of switches 330A–B to enable and latch conduction from node 310 to one of respective nodes 340A–B in only a single quadrant of the current vs. voltage graph. In one example, a negative trigger current to, or a current sink from, each of the single-quadrant thyristors 330A–B couples the large positive voltage associated with the defibrillation energy at node 310 to a respective one of electrodes 120A–B.

Single-quadrant thyristors of the type used for the various embodiments of the invention are also capable of withstanding rapid dV/dt transitions (e.g., 300 V/μs minimum). Rapid voltage versus time transitions (dV/dt) during defibrillation energy delivery occur at nodes 120A and/or 120B during turn-on and/or turn-off of pull-down switches 335A and/or 335B. Because such single-quadrant thyristors are designed to 1) withstand such dV/dt transitions; 2) provide high voltage blocking capabilities (e.g., 1200V minimum); and 3) conduct/latch in only one quadrant (e.g., quadrant III), additional semiconductor devices in series with triac/thyristor devices may be eliminated. This elimination of such series components in the defibrillation energy delivery circuit 305 may reduce the number of processing steps, reduce cost and reduce the physical size of the implantable cardiac rhythm management device.

FIG. 3 also illustrates triggering devices 370A–B, as discussed above. In one embodiment, triggering devices 370A–B include current-limiting switches such as, for example, high voltage n-channel field-effect transistors (FETs) that, when turned on by control signals S3 and S4, function in their saturation region of operation. Unlike typical FET designs, which provide high drain-source current in saturation, the present triggering devices 370A–B of one embodiment are designed with an effective low transconductance, which provides a relatively low drain-source current in saturation.

In one embodiment, this effective low transconductance is obtained by enabling for conduction a preselected number of available parallel conducting channels in triggering devices 370A–B to obtain the desired transconductance. In one example, triggering devices 370A–B are power metal-oxide-semiconductor FETs (MOSFETs) with vertically oriented conducting channels. A gate and source are associated with a first side of the semiconductor substrate of triggering devices 370A–B, and a drain is associated with an opposing second side of the semiconductor substrate of triggering devices 370A–B. A vertical channel is formed through the substrate between source and drain under control by the gate. By fabricating the power MOSFET with a plurality of drain-to-source channels, a plurality of vertical conducting channels become available. By selecting a predetermined number of the vertical channels for activation by the associated gate, a desired transconductance can be obtained.

The desired transconductance is achieved, based on the turn-on gate voltage (e.g., approximately between 10 Volts and 12 Volts) provided by control circuit 345, to provide the desired trigger current to latch the single-quadrant thyristor switches 330A–B into a conducting and latched state. In one embodiment, the first and second current-limiting switch triggering devices 370A–B each sink triggering currents from the respective first and second single-quadrant thyristor switches 330A–B of approximately between 100 and 235 milliamperes, inclusive, such that thyristor switches 330A–B latch into their conductive states. As an example, a single-quadrant thyristor switch may have a nominal triggering current of approximately 80 milliamperes required to latch into its conductive state. Its associated triggering device may be specified to have an engineering margin such that the triggering device produces a triggering current in excess of the nominal value, e.g., the triggering device may sink triggering currents of approximately 100 milliamperes in this example. In one particular embodiment, each of current-limiting FET switches 370A–B provides an on-state forward transconductance of less than or equal to approximately 45 milliSiemens. In any case, the first and second current-limiting switch triggering devices 370A and 370B are selected to achieve sufficient current sink at a given gate drive to trigger their respective thyristor switch 330A and 330B, respectively.

In FIG. 3, current-limiting FETs 370A–B are modeled as gain-degenerated devices that include respective source-degeneration resistors 375A–B. It is understood, however, that in one embodiment, source-degeneration resistors 375A–B do not represent resistors separate and distinct from devices 370A–B, but merely represent the on-state integrated source resistance associated with each of current-limiting FETs 370A–B. The on-state source resistance and/or forward transconductance is selected by enabling a predetermined number of available parallel conducting channels, as discussed above. By using triggering devices 370A–B that are inherently current-limiting, the need for additional circuits to perform such current-limiting functions is avoided. This reduces the number of electronic components required for energy delivery circuit 305, which may further reduce the number of assembly processing steps, reduce cost and reduce the physical size of the implantable cardiac rhythm management device.

In one embodiment, defibrillation energy delivery circuit 305 also includes additional electronic components, such as for determining defibrillation lead impedance. One example of using such additional electronic components for determining defibrillation lead impedance is described in U.S. patent application Ser. No. 09/236,911 to Linder et al., filed Jan. 25, 1999, which is commonly assigned and incorporated herein by reference.

Conclusion

This document describes, among other things, portions of a cardiac rhythm management system including an implantable cardiac rhythm management device that includes a defibrillation energy delivery circuit. The defibrillation energy delivery circuit provides high side energy delivery through a single-quadrant thyristor switch that is triggered by a current-limiting transistor switch. The defibrillation energy delivery circuit requires fewer electronic components, reducing the size and/or cost of the implantable cardiac rhythm management device. For example, the single-quadrant thyristor, designed to conduct and latch in only one quadrant (e.g., quadrant III) and having appropriate dV/dt and voltage blocking capabilities, may eliminate the need for additional series-coupled semiconductor devices. In another example, current-limiting is designed into, or inherent in, the semiconductor device triggering the single-quadrant thyristor, thereby eliminating the need for additional current-limiting circuits.

It is to be understood that the above description is intended to be illustrative, and not restrictive. Many other embodiments will be apparent to those of skill in the art upon reviewing the above description. For example, while the various embodiments referred to specific values of voltages, transconductance, triggering currents, etc., such values are at the discretion of the designer and could include values outside the range of the specific examples given. The scope of the invention should, therefore, be determined with reference to the appended claims, along with the full scope of equivalents to which such claims are entitled.

What is claimed is:

1. An energy delivery circuit, comprising:
    a first input terminal adapted to be connected to a first power supply;
    a second input terminal adapted to be connected to a second power supply;
    a first output terminal;
    a second output terminal;
    a first power-supply-coupling switch coupled between the first input terminal and the first output terminal, wherein the first power-supply-coupling switch is adapted to latch conduction between a voltage from the first power supply to the first output terminal in only a single quadrant of a current versus voltage graph;
    a second power-supply-coupling switch coupled between the first input terminal and the second output terminal, wherein the second power-supply-coupling switch is adapted to latch conduction between a voltage from the first power supply to the second output terminal in only a single quadrant of a current versus voltage graph;
    a first trigger switch coupled to the first power-supply-coupling switch to couple the high voltage from the first power supply to the first output terminal; and
    a second trigger switch coupled to the second power-supply-coupling switch to couple the high voltage from the first power supply to the second output terminal.

2. The circuit of claim 1, wherein the first power-supply-coupling switch is a first single-quadrant thyristor and the second power-supply coupling switch is a second single-quadrant thyristor.

3. The circuit of claim 2, wherein the single-quadrant thyristors are adapted to only latch conduction between the voltage from the first power supply to the first output terminal in a third quadrant.

4. The circuit of claim 1, wherein both the first trigger switch and the second trigger switch includes a plurality of available conducting channels of which a preselected number of the conducting channels are enabled for conduction.

5. The circuit of claim 1, further comprising:
    a third power-supply-coupling switch coupled between the second input terminal and the first output terminal; and
    a fourth power-supply-coupling switch coupled between the second input terminal and the second output terminal.

6. The circuit of claim 5, wherein the first power-supply-coupling switch includes a first single-quadrant thyristor and the second power-supply-coupling switch includes a second single-quadrant thyristor, and both the third and fourth power-supply-coupling switches include insulated gate bipolar transistors (IGBTs).

7. The circuit of claim 6, wherein the first single-quadrant thyristor is directly connected to the first output terminal and the second single-quadrant thyristor is directly connected to the second output terminal.

8. A cardiac rhythm management device, comprising:
    a controller;
    at least one lead having at least one electrode; and
    at least one therapy circuit coupled to the controller and to the at least one electrode, the at least one therapy circuit including:
        a first input terminal adapted to be connected to a first power supply;
        a first output terminal; and
        a first power-supply-coupling switch coupled between the first input terminal and the first output terminal, wherein the first power-supply-coupling switch is adapted to latch conduction between a voltage from the first power supply to the first output terminal in only a single quadrant of a current versus voltage graph.

9. The device of claim 8, further comprising at least one sensing circuit coupled to the controller and to the at least one electrode.

10. The device of claim 8, wherein the device is programmable to deliver monophasic energy through the at least one electrode.

11. The device of claim 8, wherein the device is programmable to deliver biphasic energy through the at least one electrode.

12. The device of claim 8, wherein the device is programmable to deliver multiphasic energy through the at least one electrode.

13. The device of claim 8, wherein the first power-supply-coupling switch is a single-quadrant thyristor.

14. The circuit of claim 13, wherein the single-quadrant thyristor is adapted to only latch conduction between the high voltage from the first power supply to the first output terminal in a third quadrant.

15. A cardiac rhythm management device, comprising:
    a first power supply;
    a second power supply;
    a controller;
    at least one lead having at least one electrode; and
    at least one therapy circuit coupled to the controller and to the at least one electrode, the at least one therapy circuit having the form of an H-bridge circuit, including:
        a first input terminal coupled to the first power supply;
        a second input terminal coupled to the second power supply;
        a first output terminal;
        a second output terminal;
        a first single-quadrant thyristor coupled between the first input terminal and the first output terminal;
        a first switch coupled to the controller and to a gate terminal of the first thyristor for sinking a triggering current;
        a second single-quadrant thyristor coupled between the first input terminal and the second output terminal; and
        a second switch coupled to the controller and to a gate terminal of the second thyristor for sinking a triggering current.

16. The device of claim 15, wherein both the first single-quadrant thyristor and the second single-quadrant thyristor are adapted to only latch conduction in a third quadrant.

17. The device of claim 15, wherein the first switch and the second switch include a plurality of available conducting channels of which a preselected number of the conducting channels are enabled for conduction.

18. A method for forming a cardiac rhythm management device, comprising:
    coupling a first power-supply-coupling switch between a first power supply and a first output terminal, wherein the first power supply switch is adapted to latch current in only a single quadrant of a current versus voltage graph; and
    comprising coupling a first trigger switch to the first power-supply-coupling switch.

19. The method of claim 18, further comprising:
    coupling a second power-supply-coupling switch between the first power supply and a second output terminal; and coupling a second trigger switch to the second power supply coupling switch.

20. The method of claim 19, wherein coupling a first trigger switch and coupling a second trigger switch include coupling devices with a plurality of conducting channels of which a preselected number of the conducting channels are enabled for conduction.

21. The method of claim 19, further comprising coupling a controller to the first trigger switch and the second trigger switch.

22. The method of claim 21, wherein coupling a controller includes coupling a controller adapted to be programmed to deliver monophasic energy.

23. The method of claim 21, wherein coupling a controller includes coupling a controller adapted to be programmed to deliver biphasic energy.

24. The method of claim 21, wherein coupling a controller includes coupling a controller adapted to be programmed to deliver multiphasic energy.

25. The method of claim 19, further comprising:
coupling a third power-supply-coupling switch between the first output node and the second power supply; and
coupling a fourth power-supply-coupling switch between the second output node and the second power supply.

26. The method of claim 25, wherein coupling a third power-supply-coupling switch and coupling a fourth power-supply-coupling switch includes coupling insulated gate bipolar transistors (IGBTs).

27. The method of claim 19, further comprising coupling at least one electrode in at least one lead to one of the first output and the second output.

* * * * *